US010981129B2

(12) United States Patent
Kapre et al.

(10) Patent No.: US 10,981,129 B2
(45) Date of Patent: Apr. 20, 2021

(54) DOUBLE CHAMBER DEVICE FOR POINT OF USE MIXING

(71) Applicant: Inventprise, LLC, Redmond, WA (US)

(72) Inventors: Subhash V. Kapre, Redmond, WA (US); Kapil Subhash Kapre, Redmond, WA (US)

(73) Assignee: Inventprise, LLC, Redmond, WA (US)

( * ) Notice: Subject to any disclaimer, the term of this patent is extended or adjusted under 35 U.S.C. 154(b) by 447 days.

(21) Appl. No.: 16/043,400

(22) Filed: Jul. 24, 2018

(65) Prior Publication Data

US 2019/0039035 A1    Feb. 7, 2019

Related U.S. Application Data

(60) Provisional application No. 62/541,977, filed on Aug. 7, 2017.

(51) Int. Cl.
| | |
|---|---|
| *B01F 15/00* | (2006.01) |
| *B01F 15/02* | (2006.01) |
| *B01F 3/12* | (2006.01) |
| *B05C 11/10* | (2006.01) |
| *A61J 1/20* | (2006.01) |
| *B01F 13/00* | (2006.01) |
| *A61M 5/24* | (2006.01) |
| *A61M 5/315* | (2006.01) |
| *A61M 5/34* | (2006.01) |

(Continued)

(52) U.S. Cl.
CPC .......... *B01F 15/0087* (2013.01); *A61J 1/201* (2015.05); *A61J 1/2027* (2015.05); *A61J 1/2048* (2015.05); *A61J 1/2093* (2013.01); *A61M 5/2448* (2013.01); *A61M 5/3129* (2013.01); *A61M 5/31596* (2013.01); *A61M 5/34* (2013.01); *B01F 3/12* (2013.01); *B01F 13/0023* (2013.01); *B01F 15/00506* (2013.01); *B01F 15/0237* (2013.01); *B05C 11/10* (2013.01); *B05C 17/00563* (2013.01)

(58) Field of Classification Search
CPC .............. B01F 15/0087; B01F 15/0237; B01F 15/00506; B01F 3/12; B01F 13/0023; A61M 5/2448; A61M 5/31596; A61M 5/34; A61M 5/3129; B05C 17/00563; B05C 11/10; A61J 1/2027; A61J 1/2093; A61J 1/2048; A61J 1/201
See application file for complete search history.

(56) References Cited

U.S. PATENT DOCUMENTS

| | | | |
|---|---|---|---|
| 4,159,570 A | 7/1979 | Baskas | |
| 4,551,135 A * | 11/1985 | Gorman | ............. A61B 17/8816 433/80 |

(Continued)

OTHER PUBLICATIONS

Search Report and Opinion for Application No. PCT/US2018/43379 dated Oct. 23, 2018.

*Primary Examiner* — Tony G Soohoo
(74) *Attorney, Agent, or Firm* — Remenick PLLC (57) ABSTRACT

Disclosed is a double chamber container. The first chamber comprises a stopper coupled to a first end and a cover coupled to a second end. The second chamber comprises a plunger coupled to one end and an open second end. The first chamber is coupled to the second chamber such that the first end of the first chamber is coupled to the second end of the second chamber.

19 Claims, 8 Drawing Sheets

(51) Int. Cl.
*A61M 5/31* (2006.01)
*B05C 17/005* (2006.01)

(56) References Cited

U.S. PATENT DOCUMENTS

| | | | | |
|---|---|---|---|---|
| 4,820,306 | A | * | 4/1989 | Gorman ............. A61B 17/8816 128/898 |
| 5,435,076 | A | * | 7/1995 | Hjertman ............. A61M 5/284 34/296 |
| 5,665,068 | A | | 9/1997 | Takamura |
| 5,716,338 | A | * | 2/1998 | Hjertman ............. A61M 5/2448 604/89 |
| 6,349,850 | B1 | * | 2/2002 | Cheikh ................. A61M 5/002 222/1 |
| 6,386,872 | B1 | * | 5/2002 | Mukasa ................... A61C 5/64 206/219 |
| 9,016,925 | B2 | * | 4/2015 | Faccioli ............. B01F 15/0206 366/130 |
| 2006/0178638 | A1 | | 8/2006 | Reynolds |
| 2019/0039035 | A1 | * | 2/2019 | Kapre ................. A61M 5/3129 |

* cited by examiner

DOUBLE CHAMBER DEVICE FOR POINT OF USE MIXING

REFERENCE TO RELATED APPLICATIONS

This application claims priority to U.S. Provisional Application No. 62/541,977 filed Aug. 7, 2017, the entirety of which is hereby specifically incorporated by reference.

BACKGROUND

1. Field of the Invention

The invention is directed to a container for holding two matters. In particular, the invention is directed to a container for separately holding two matters to be mixed at the point of use.

2. Background of the Invention

In many industries two or more matters need to be maintained separately until the point of use for a variety of reasons. Matters can include solids, liquids, or gasses. For example, certain epoxies are made by mixing two components at the time of use. If the components are mixed prematurely, the epoxy might harden prior to application. Similarly, to obtain better potency, certain medical drugs are preferably mixed at the time of administration. If the drug components are mixed prematurely, the drug may not have the desired effect. Furthermore, the mixed drug may degrade when exposed to air. Another example is in the food industry where if ingredients are mixed too early, the taste or freshness may degrade to undesirable levels prior to consumption.

Therefore, there is a need for a container that can maintain two components separately until the desired time and location for mixing the components. Additionally, it is desirable to be able to mix the components without exposing them to the environment.

SUMMARY OF THE INVENTION

The present invention overcomes the problems and disadvantages associated with current strategies and designs and provides new tools and methods of maintaining two components separately until the point of use.

One embodiment of the invention is directed to a double chamber container. The container comprises a first chamber, the first chamber comprising a stopper coupled to a first end and a cover coupled to a second end, the first chamber adapted to hold a first matter. The container further comprises a second chamber, the second chamber comprising a plunger coupled to one end and an open second end, the second chamber adapted to hold a second matter separate from the first matter. The first chamber is coupled to the second chamber such that the first end of the first chamber is coupled to the second end of the second chamber. As the plunger is depressed, the second matter is forced into the first chamber and is mixed with the first matter.

In a preferred embodiment, the first chamber further comprises at least one side channel. Preferably, the at least one side channel is adapted to allow fluid to flow around the stopper when the stopper is adjacent to the at least one side channel. The first and second chambers are preferably coupled together with an ultrasonic seal. Preferably, the cover is a luer-lock tip and the luer-lock tip is adapted to receive a needle or a dispensing tip. Preferably, the double chamber container is a single use device. In a preferred embodiment, cover is a self-healing stopper and the self-healing stopper is adapted to be pierced by a needle multiple times. Preferably, double chamber container is a multi-use device.

In a preferred embodiment, the first chamber contains a first matter and the second chamber contains a second matter, wherein the first matter and the second matter mix upon the plunger forcing the second matter through the second chamber, into the stopper, and moving the stopper and the second matter into the first chamber. Upon mixing, the contents of the container is preferably a vaccine, a medication, or an epoxy. Preferably, the first matter is a lyophilized material and the second matter is a liquid diluent. Preferably, the contents are sealed from exposure to the environment.

Another preferred embodiment is directed to a method of assembling a double chamber container. The method comprises the steps of inserting a stopper into a first end of a first chamber, filling the first chamber with a first matter, coupling a cover to a second end of the first chamber, inserting a plunger into a first end of a second chamber, filling the second chamber with a second matter, and coupling the first end of the first chamber to a second end of the second chamber.

Preferably the method further comprises processing the first matter prior to coupling the first and second chambers. In a preferred embodiment, the processing is a lyophilizing process. Preferably, the coupling step is comprised of ultrasonic sealing. Preferably, the cover is a luer-lock tip and the luer-lock tip is adapted to receive a needle or a dispensing tip. The double chamber container is preferably a single use device. In a preferred embodiment, the cover is a self-healing stopper and the self-healing stopper is adapted to be pierced by a needle multiple times. Preferably, the double chamber container is a multi-use device.

Other embodiments and advantages of the invention are set forth in part in the description, which follows, and in part, may be obvious from this description, or may be learned from the practice of the invention.

DESCRIPTION OF THE DRAWINGS

The invention is described in greater detail by way of example only and with reference to the attached drawing, in which.

DESCRIPTION OF THE INVENTION

As embodied and broadly described herein, the disclosures herein provide detailed embodiments of the invention.

However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

A problem in the art capable of being solved by the embodiments of the present invention is maintaining matters separately until the point of use. It has been surprisingly discovered that two or more abutting cups can be sealed together to create a container having compartments for multiple matters to be mixed at the point of use.

Figure 1:
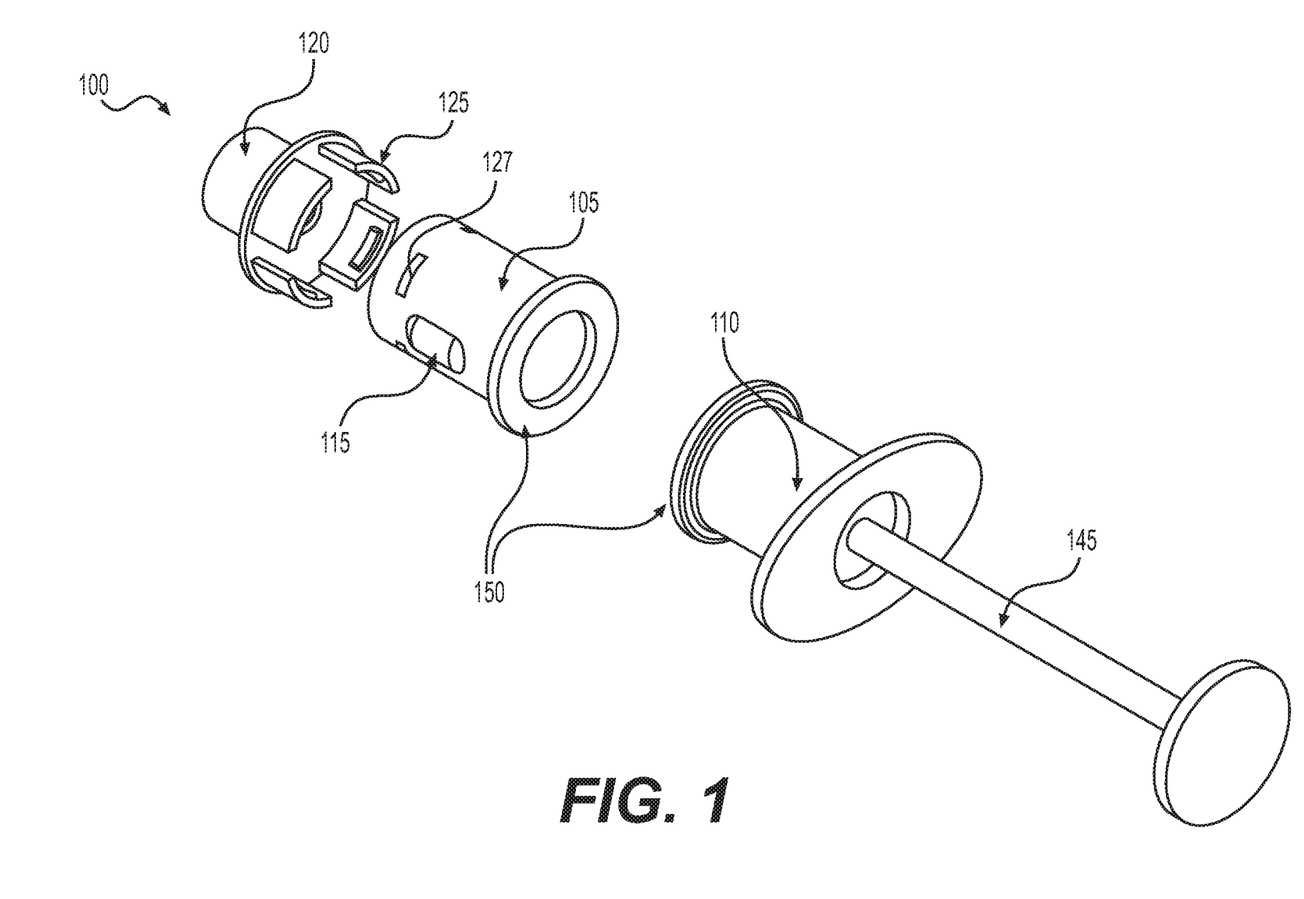
FIG. 1 depicts an exploded view of an embodiment of a single dose container.

FIG. 1 depicts an exploded side view of an embodiment of a single dose container 100. Container 100 is preferably comprised of a first chamber 105 and a second chamber 110. While two chambers or receptacles are shown, container 100 can be made of three or more chambers depending on the number of matters to be held separately. Each chamber 105 and 110 is preferably capable of holding a matter. For example, each chamber 105 and 110 can hold a liquid, solid, or gas. Additionally, each chamber 105 and 110 can hold a combination of matters. For example, each chamber 105 and 110 can hold two or more liquids, two or more solids, two or more gasses, or any combination of liquids, solids, and gasses. The matters can be a suspension, a colloid, a solution, or otherwise mixed. Moreover, upon mixing, the matters in chambers 105 and 110 can form a liquid, solid, gas, suspension, colloid, solution, or other mix. The matters in one or more of chambers 105 and 110 can be maintained under pressure, at atmospheric pressure, in a vacuum, or be unpressurized. Upon mixing, a chemical reaction may or may not occur. The contents of container 100 may have to be vigorously shaken to properly mix. The final mixture may be a vaccine, another medicine, an epoxy, a food, a drink, a cleaning product, or another mixture.

Chambers 105 and 110 are preferably cylindrical tubes with openings at each end. However, outer chambers 105 and 110 can have another shape, for example a cuboid, a cone, a pyramid, or another shape. Furthermore, chambers 105 and 110 may be the same or different shapes. Chambers 105 and 110 may be able to contain the same volume or different volumes.

Chambers 105 and 110 are preferably a plastic material molded into the desired shape. For example, chambers 105 and 110 can be roto-molded, injection molded, blow molded, or welded together. However, chambers 105 and 110 can be made of one or more different materials. For example, glass, metals, fabrics, rubbers, woods, or other natural or manmade materials. The choice of material may depend on the intended contents of chambers 105 and 110. In certain embodiments, the interior surface of chambers 105 and 110 may be coated. For example, the surface may be coated with plastic, wax, or another material that will not interact with the intended contents of the chamber. Chambers 105 and 110 may be of the same material or different materials.

Chamber 105 preferably has one or more side channels 115 to promote fluid flow, as described herein. Furthermore, chamber 105 preferably has an end cap. In the embodiment shown in FIG. 1, end cap is preferably a luer-lock tip 120 adapted to receive a needle for injecting the solution or a plastic or rubber tip for oral delivery of the solution. Luer-lock tip 120 may be a female or male receptacle, additionally, luer-lock tip 120 may be vented. Preferably luer-lock tip 120 is adapted to fit over the end of chamber 105 and snap into place with tabs 125. Tabs 125 may fit into slots or recesses 127 in chamber 105. In other embodiments, luer-lock tip 120 may be secured by friction, threading, screws, bolts, adhesives, or other coupling devices.

Figure 2:
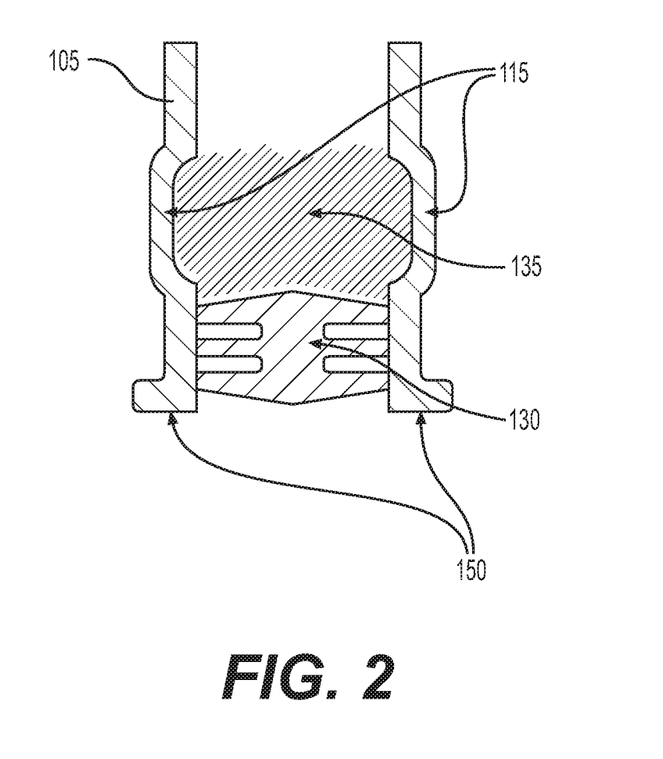
FIG. 2 depicts a cut-away view of an embodiment of one chamber of the container shown in FIG. 1.

FIG. 2 depicts a cut away view of chamber 105. Preferably, chamber 105 is filled with a matter 135. In the preferred embodiment, matter 135 is a lyophilized (or freeze dried) material. However, matter 135 may be any liquid, solid, or gas. At the end of chamber 105 opposite the luer-lock tip 120, preferably a stopper 130 is inserted. Preferably, stopper 130 has a diameter equal to the inner diameter of chamber 105 so that none of matter 135 leaks past stopper 130. Additionally, the inner diameter of side channels 115 are preferably larger than the diameter of stopper 130 so that material can flow around stopper 130 when stopper 130 is adjacent to side channels 115.

Figures 3, 4:
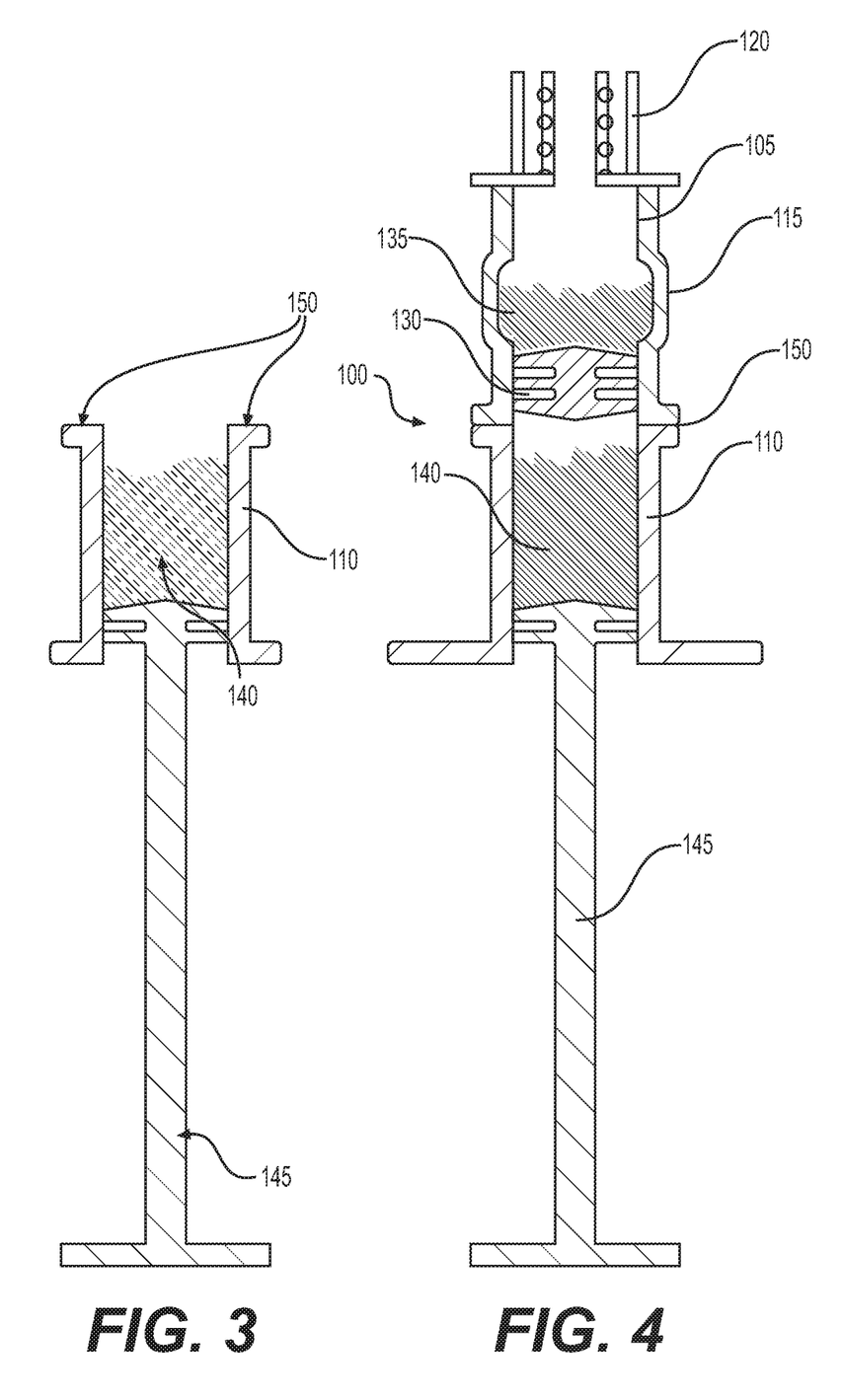
FIG. 3 depicts a cut-away view of an embodiment of a second chamber of the container shown in FIG. 1.
FIG. 4 depicts a cut-away view of an embodiment of the assembled container shown in FIG. 1.

FIG. 3 depicts a cut away view of chamber 110. Preferably, chamber 110 is filled with a matter 140. Preferably, matter 140 is a diluent, however, matter 140 may be any liquid, solid, or gas. Preferably chamber 110 has a plunger 145 positioned within one end and the second end is open. Plunger 145 preferably is a rod with a first end with a seal having a diameter equal to the inner diameter of chamber 110 so that none of matter 140 leaks past the seal and plunger 145 is able to push matter 140 out of chamber 110 into chamber 105. The second end of plunger 145 preferably has a top adapted to fit a finger or thumb.

Figure 5A:
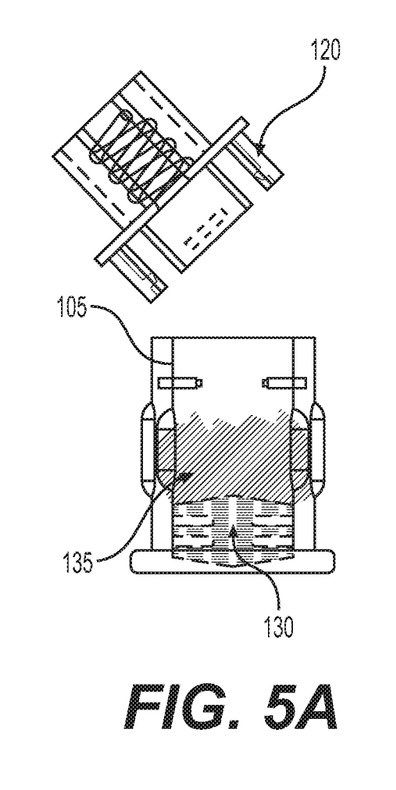
FIGS. 5A-C depict cut-away views of an embodiment of filling the first chamber of the container shown in FIG. 1.
Figure 5B:
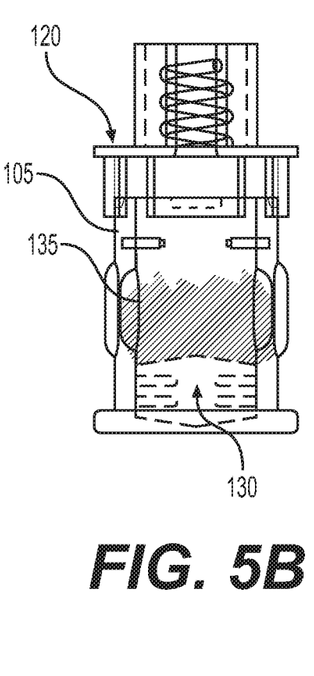
Figure 5C:
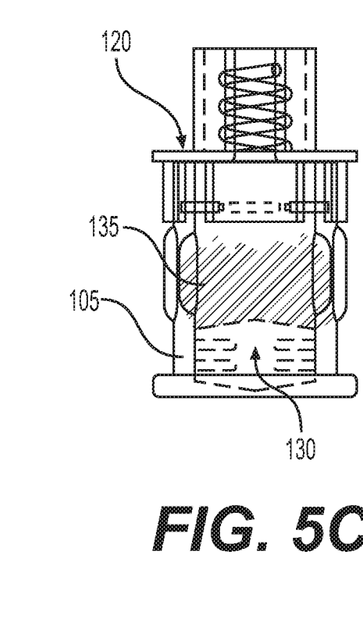

FIG. 4 depicts a cut away of the assembled container 100. Preferably, chambers 105 and 110 are sealed together (for example using ultrasonic heating, laser welding, adhesive, screwed together, latches, bolts, brads, welds, or otherwise coupled) to create a water and/or air tight connection 150. FIGS. 5A-C depict an embodiment of the steps of filling and sealing chamber 105. In FIG. 5A, stopper 130 is preferably inserted into chamber 105. Chamber 105 is then filled with matter 135. In FIG. 5B, luer-lock tip 120 is preferably partially placed on chamber 105. At this point, chamber 105 may be placed in a lyophiliser, a centrifuge, a sanitizer, or another device to process matter 135. In other embodiments, matter 135 does not need processing. Once matter 135 is processed, in FIG. 5C, luer-lock tip 120 is fully seated onto chamber 105, thereby sealing matter 135 within chamber 105. Simultaneously or in succession, chamber 110 may have plunger 145 inserted therein and be filled with matter 140. Once both chambers 105 and 110 are filled and any necessary processing is completed, the stopper end of chamber 105 is preferably placed over the open end of chamber 110 and the two chambers are sealed together.

Figure 6A:
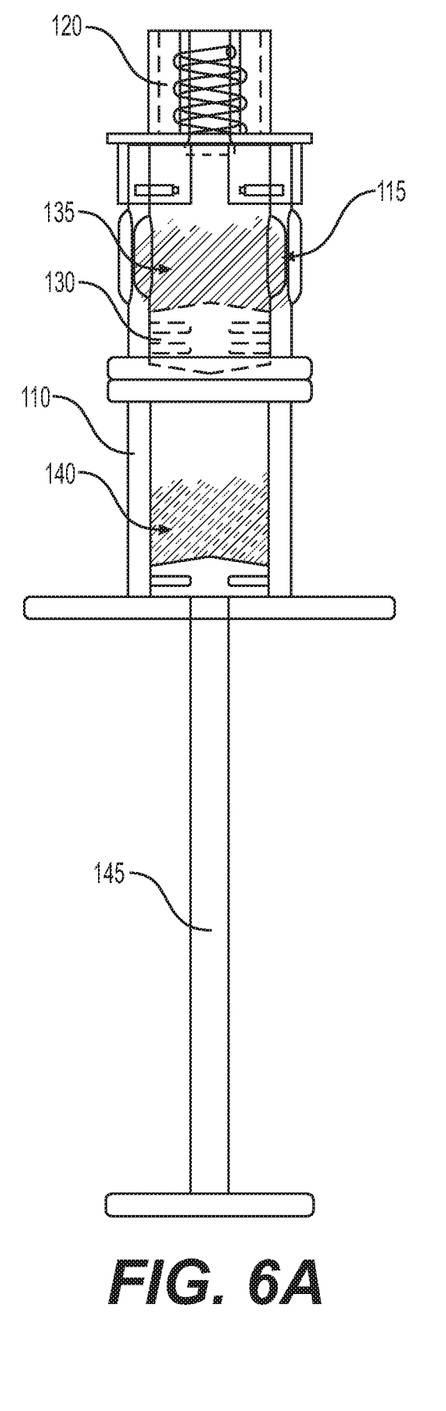
FIGS. 6A-B depict views of the container shown in FIG. 1 in use.
Figure 6B:
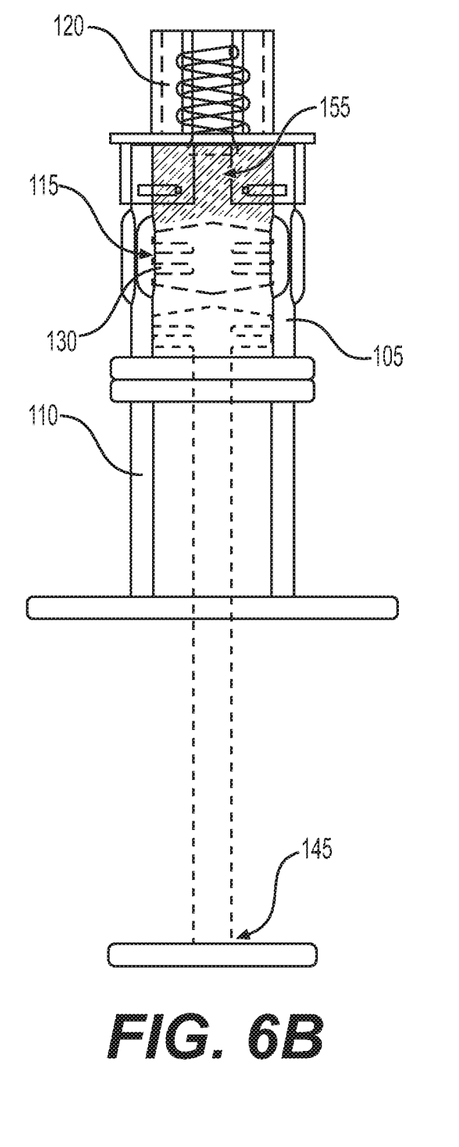

As shown in FIGS. 6A and 6B, in use, matters 135 and 140 are held separately in chambers 105 and 110, respectively, until the time of use. At the time of use, plunger 145 is depressed and pushes matter 140 into stopper 130. As plunger 145 continues to be depressed, stopper 130 is pushed adjacent to side channels 115, which allows matter 140 to bypass stopper 130 and mix with matter 135. Matters 135 and 140 may instantly combine to create mixture 155, may combine within a specific timeframe, or may need to be shaken to combine. Once combined, plunger 145 can continue to be depressed thereby forcing mixture 155 out of container 100 through luer-lock tip 120 and into either a needle or another tip.

Figures 7A, 7B:
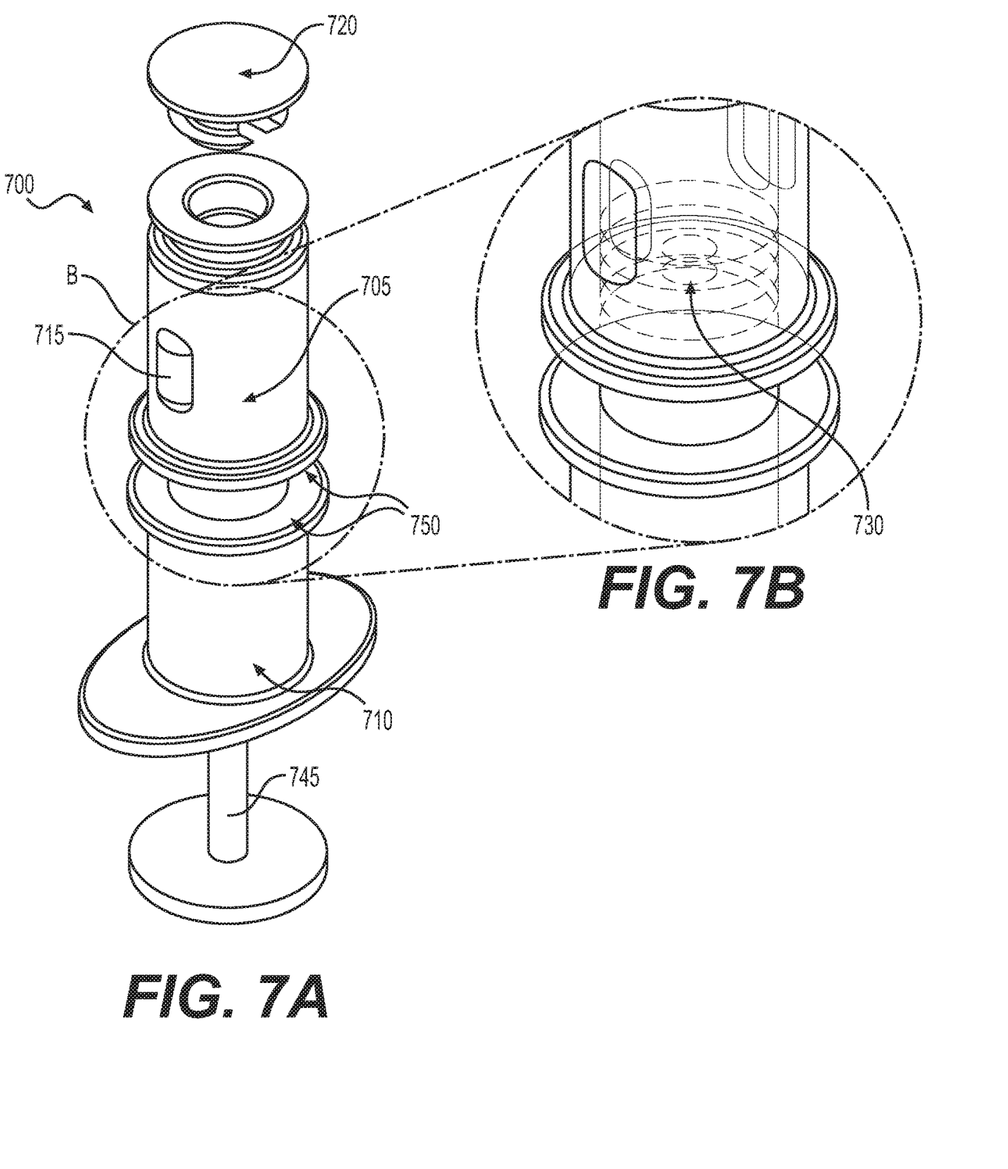
FIG. 7A-B depict exploded views of an embodiment of a multi dose container.

FIGS. 7A and 7B depict exploded side views of an embodiment of a multi-dose container 700. Container 700 is similar in construction to container 100 (similar numbers are used to indicate similar components). Container 700 is preferably comprised of a first chamber 705 and a second chamber 710. While two chambers or receptacles are shown, container 700 can be made of three or more chambers depending on the number of matters to be held separately. Each chamber 705 and 710 is preferably capable of holding a matter. For example, each chamber 705 and 710 can hold a liquid, solid, or gas. Additionally, each chamber 705 and 710 can hold a combination of matters. For example, each chamber 705 and 710 can hold two or more liquids, two or more solids, two or more gasses, or any combination of liquids, solids, and gasses. The matters can be a suspension, a colloid, a solution, or otherwise mixed. Moreover, upon mixing, the matters in chambers 705 and 710 can form a liquid, solid, gas, suspension, colloid, solution, or other mix. The matters in one or more of chambers 705 and 710 can be maintained under pressure, at atmospheric pressure, in a vacuum, or be unpressurized. Upon mixing, a chemical reaction may or may not occur. The contents of container 700 may have to be vigorously shaken to properly mix. The final mixture may be a vaccine, another medicine, an epoxy, a food, a drink, a cleaning product, or another mixture.

Chambers 705 and 710 are preferably cylindrical tubes with openings at each end. However, chambers 705 and 710 can have another shape, for example a cuboid, a cone, a pyramid, or another shape. Furthermore, chambers 705 and 710 may be the same or different shapes. Chambers 705 and 710 may be able to contain the same volume or different volumes.

Chambers 705 and 710 are preferably a plastic material molded into the desired shape. For example, chambers 705 and 710 can be roto-molded, injection molded, blow molded, or welded together. However, chambers 705 and 710 can be made of one or more different materials. For example, glass, metals, fabrics, rubbers, woods, or other natural or manmade materials. The choice of material may depend on the intended contents of chambers 705 and 710. In certain embodiments, the interior surface of chambers 705 and 710 may be coated. For example, the surface may be coated with plastic, wax, or another material that will not interact with the intended contents of the chamber. Chambers 705 and 710 may be of the same material or different materials. Chamber 705 preferably has one or more side channels 715 to promote fluid flow, as described herein. Furthermore, chamber 705 preferably has an end cap. In the embodiment shown in FIG. 7A, end cap is preferably a pierceable stopper 720 adapted to be pierced by a needle for removing multiple doses. Stopper 720 may be rubber, cork, or another self-healing material. Preferably, stopper 720 is friction fit into chamber 705, however, stopper 720 may be screwed, bolted, affixed with adhesive or otherwise coupled to chamber 705. Preferably, stopper 720 is vented.

Figure 8A:
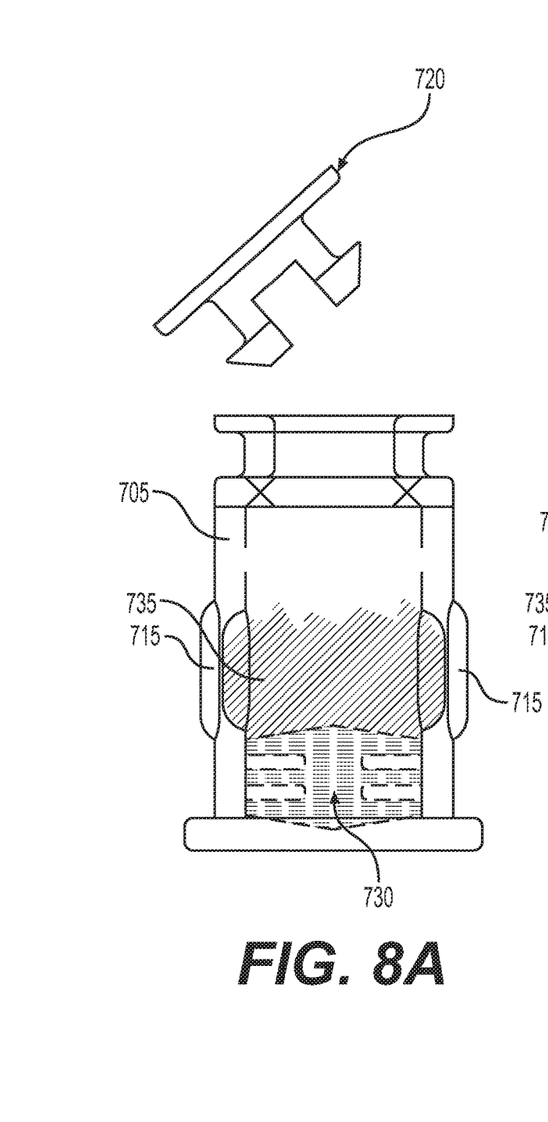
FIGS. 8A-C depict cut-away views of an embodiment of filling the first chamber of the container shown in FIG. 7.
Figure 8B:
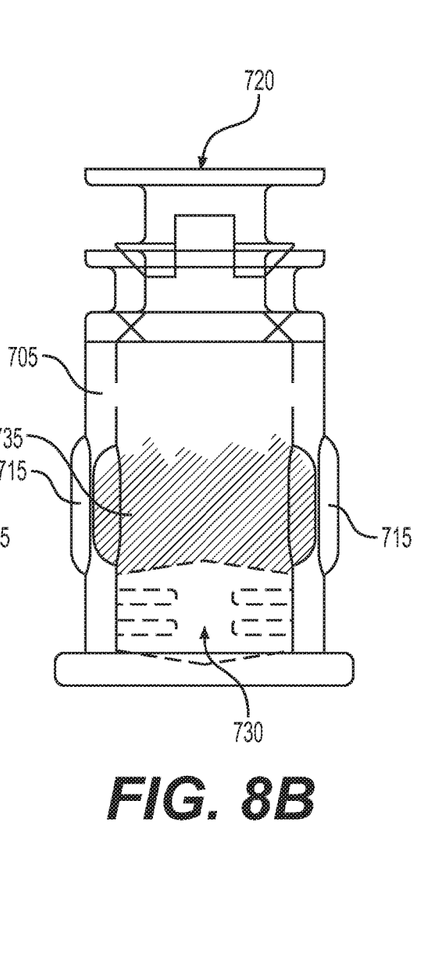
Figure 8C:
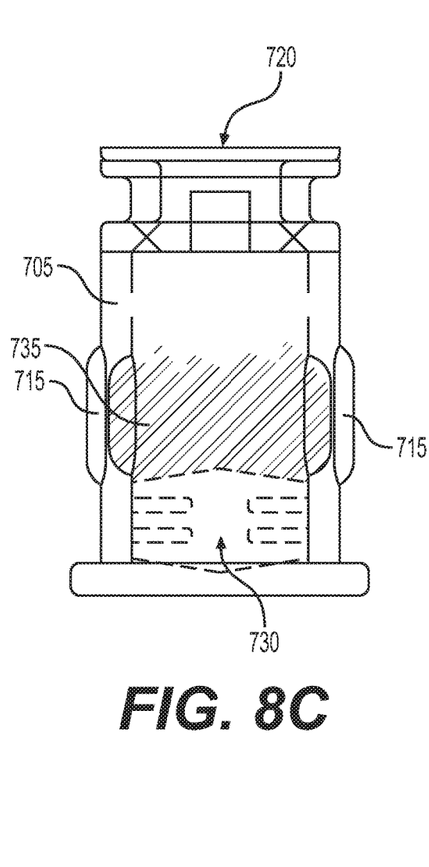

As shown in FIGS. 8A-C, preferably, chamber 705 is filled with a matter 735. In the preferred embodiment, matter 735 is a lyophilized (or freeze dried) material. However, matter 735 may be any liquid, solid, or gas. At the end of chamber 705 opposite the stopper 720, preferably a movable stopper 730 is inserted. Preferably, stopper 730 has a diameter equal to the inner diameter of chamber 705 so that none of matter 735 leaks past stopper 730. Additionally, the inner diameter of side channels 715 are preferably larger than the diameter of stopper 730 so that material can flow around stopper 730 when stopper 730 is adjacent to side channels 715.

Figure 9A:
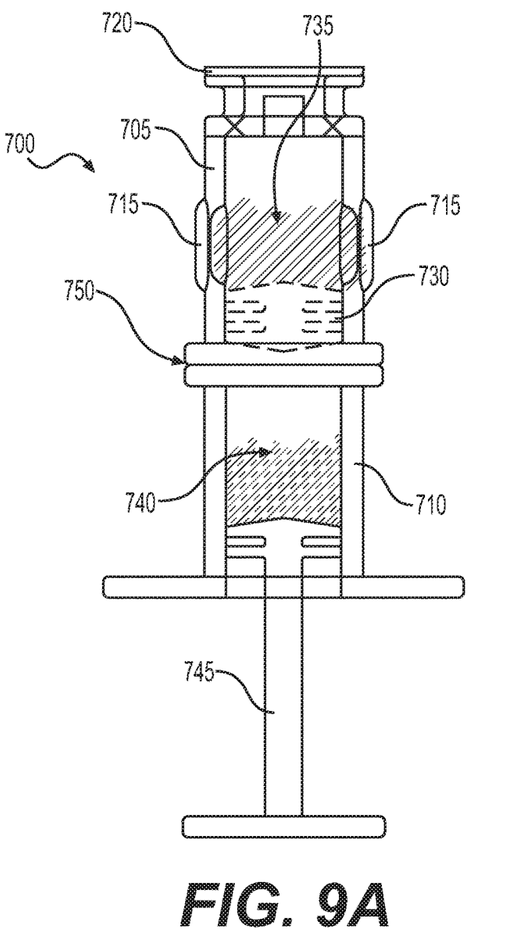
FIGS. 9A-B depict views of the container shown in FIG. 7 in use.
Figure 9B:
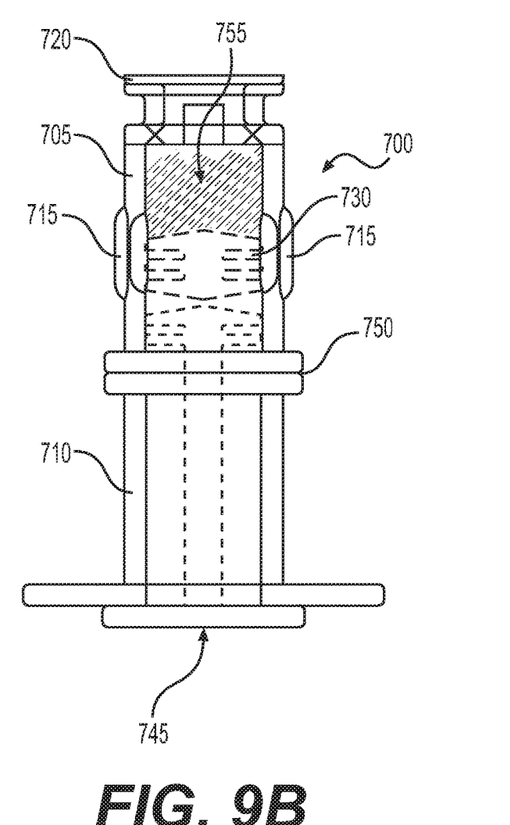

As shown in FIGS. 9A-B, preferably, chamber 710 is filled with a matter 740. Preferably, matter 740 is a diluent, however, matter 740 may be any liquid, solid, or gas. Preferably chamber 710 has a plunger 745 positioned within one end and the second end is open. Plunger 745 preferably is a rod with a first end with a seal having a diameter equal to the inner diameter of chamber 710 so that none of matter 740 leaks past the seal and plunger 745 is able to push matter 740 out of chamber 710 into chamber 705. The second end of plunger 745 preferably has a top adapted to fit a finger or thumb. Preferably, the rod of plunger 745 is shorter than the rod of plunger 145.

Preferably, chambers 705 and 710 are sealed together (for example using ultrasonic heating, laser welding, adhesive, screwed together, latches, bolts, brads, welds, or otherwise coupled) to create a water and/or air tight connection 750. FIGS. 8A-C depict an embodiment of the steps of filling and sealing chamber 705. In FIG. 8A, stopper 730 is preferably inserted into chamber 705. Chamber 705 is then filled with matter 735. In FIG. 8B, cover 720 is preferably partially placed on chamber 705. At this point, chamber 705 may be placed in a lyophiliser, a centrifuge, a sanitizer, or another device to process matter 735. In other embodiments, matter 735 does not need processing. Once matter 735 is processed, in FIG. 8C, cover 720 is fully seated onto chamber 705, thereby sealing matter 735 within chamber 705. Simultaneously or in succession, chamber 710 may have plunger 745 inserted therein and be filled with matter 740. Once both chambers 705 and 710 are filled and any necessary processing is completed, the stopper end of chamber 705 is preferably placed over the open end of chamber 110 and the two chambers are sealed together.

As shown in FIGS. 9A and 9B, in use, matters 735 and 740 are held separately in chambers 705 and 710, respectively, until the time of use. At the time of use, plunger 745 is depressed and pushes matter 740 into stopper 730. As plunger 745 continues to be depressed, stopper 730 is pushed adjacent to side channels 715, which allows matter 740 to bypass stopper 730 and mix with matter 735. Matters 735 and 740 may instantly combine to create mixture 755, may combine within a specific timeframe, or may need to be shaken to combine. Once combined, plunger 745 is preferably fully inserted into container 700 and cannot continue to be depressed. At this point, another syringe can be used to pierce cover 720 and withdraw one or more doses of mixture 755.

Preferably, containers 100 and 700 comply to medical grade standards. Containers 100 and 700 may be single-use disposable devices or may be reusable. Alternative, portions of containers 100 and 700 may be disposable and other portions may be reusable.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:
1. A method of assembling a double chamber container, comprising:
    inserting a stopper into a first end of a first chamber;
    filling the first chamber with a first matter;
    coupling a cover to a second end of the first chamber;
    inserting a plunger into a first end of a second chamber;
    filling the second chamber with a second matter; and
    coupling the first end of the first chamber to a second end of the second chamber wherein the coupling step is comprised of ultrasonic sealing.

2. The method of claim 1, wherein the first matter is processed prior to coupling the first and second chambers.

3. The method of claim 2, wherein the processing is a lyophilizing process.

4. The method of claim 1, wherein the cover is a luer-lock tip and the luer-lock tip is adapted to receive a needle or a dispensing tip.

5. The method of claim 4, wherein the double chamber container is constructed as a single use device.

6. The method of claim 1, wherein the cover is a self-healing stopper and the self-healing stopper is adapted to be pierced by a needle multiple times.

7. The method of claim 6, wherein the double chamber container is constructed as a multi-use device.

8. A method of assembling a double chamber container, comprising:
    inserting a stopper into a first end of a first chamber;
    filling the first chamber with a first matter;
    coupling a cover to a second end of the first chamber;
    inserting a plunger into a first end of a second chamber;
    filling the second chamber with a second matter; and
    coupling the first end of the first chamber to a second end of the second chamber, wherein the cover is a luer-lock tip and the luer-lock tip is adapted to receive a needle or a dispensing tip.

9. The method of claim 8, wherein the first matter is processed prior to coupling the first and second chambers.

10. The method of claim 9, wherein the processing is a lyophilizing process.

11. The method of claim 8, wherein the coupling step is comprised of ultrasonic sealing.

12. The method of claim 8, wherein the double chamber container is constructed as a single use device.

13. The method of claim 8, wherein the cover is a self-healing stopper and the self-healing stopper is adapted to be pierced by a needle multiple times.

14. The method of claim 8, wherein the double chamber container is constructed as a multi-use device.

15. A method of assembling a double chamber container, comprising: inserting a stopper into a first end of a first chamber, filling the first chamber with a first matter: coupling a cover to a second end of the first chamber, inserting a plunger into a first end of a second chamber; filling the second chamber with a second matter; and coupling the first end of the first chamber to a second end of the second chamber, wherein the cover is a self-healing stopper and the self-healing stopper is adapted to be pierced by a needle multiple times.

16. The method of claim 15, wherein the first matter is processed prior to coupling the first and second chambers.

17. The method of claim 16, wherein the processing is a lyophilizing process.

18. The method of claim 15, wherein the coupling step is comprised of ultrasonic sealing.

19. The method of claim 15, wherein the double chamber container is constructed as a multi-use device.

* * * * *